United States Patent
Kobilka et al.

(10) Patent No.: US 10,056,553 B2
(45) Date of Patent: Aug. 21, 2018

(54) QUATERNIZED TETRAZINE-BASED DONOR-ACCEPTOR COPOLYMERS

(71) Applicant: International Business Machines Corporation, Armonk, NY (US)

(72) Inventors: Brandon M. Kobilka, Tucson, AZ (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 58 days.

(21) Appl. No.: 15/226,961

(22) Filed: Aug. 3, 2016

(65) Prior Publication Data
US 2018/0040825 A1    Feb. 8, 2018

(51) Int. Cl.
| | |
|---|---|
| *H01L 51/00* | (2006.01) |
| *C07D 471/22* | (2006.01) |
| *C08G 61/12* | (2006.01) |
| *H01L 51/42* | (2006.01) |

(52) U.S. Cl.
CPC ........ *H01L 51/0043* (2013.01); *C07D 471/22* (2013.01); *C08G 61/126* (2013.01); *H01L 51/0036* (2013.01); *C08G 2261/12* (2013.01); *C08G 2261/1424* (2013.01); *C08G 2261/228* (2013.01); *C08G 2261/3241* (2013.01); *C08G 2261/3243* (2013.01); *C08G 2261/91* (2013.01); *H01L 51/42* (2013.01)

(58) Field of Classification Search
None
See application file for complete search history.

(56) References Cited

U.S. PATENT DOCUMENTS

| | | | |
|---|---|---|---|
| 4,519,937 A * | 5/1985 | Papir ............... | C07D 261/20 252/500 |
| 8,673,183 B2 | 3/2014 | Ding et al. | |
| 8,969,508 B2 | 3/2015 | Wen et al. | |
| 9,035,015 B1 | 5/2015 | Wen et al. | |
| 9,147,853 B2 | 9/2015 | Gaudiana et al. | |
| 9,337,358 B2 | 5/2016 | Byrne et al. | |
| 2012/0007026 A1 * | 1/2012 | Ding ............... | B82Y 30/00 252/500 |
| 2013/0167929 A1 | 7/2013 | Wen et al. | |
| 2014/0124035 A1 | 5/2014 | Byrne et al. | |
| 2015/0129038 A1 | 5/2015 | Wen et al. | |

FOREIGN PATENT DOCUMENTS

WO    WO 2016010485 A1 *   1/2016  ........... C08G 61/122

OTHER PUBLICATIONS

Izuhara et al., *Poly(Pyridinium Phenylene)s: Water-Soluble N-Type Polymers*, MIT Open Access Articles, Journal of the American Chemical Society 131.49 (2009), DOI: 10.1021/ja906513u, published Nov. 19, 2009, 17 pages.

(Continued)

*Primary Examiner* — Katie L Hammer
(74) *Attorney, Agent, or Firm* — Roy R. Salvagio; Steven L. Bennett; Kennedy Lenart Spraggins LLP (57) ABSTRACT

A quaternized tetrazine-based donor-acceptor (D-A) copolymer is disclosed.

9 Claims, 10 Drawing Sheets

(56) References Cited

OTHER PUBLICATIONS

Izuhara et al., *Poly(3-hexylthiophene)-block-poly(pyridinium phenylene)s: Block Polymers of p- and n-Type Semiconductors*, MIT Department of Chemistry, Macromolecules, 2011, 44 (8), American Chemical Society, DOI: 10.1021/ma102566u, published Mar. 25, 2011, 7 pages.
Izuhara et al., *Bispyridinium-phenylene-based copolymers: low band gap n-type alternating copolymers*, Journal of Materials Chemistry, 2011, 21, DOI: 10.1039/c0jm02530e, published online Jan. 27, 2011, 6 pages.
Li et al., *Development of a New s-Tetrazine-Based Copolymer for Efficient Solar Cells*, Journal of the American Chemical Society, 2010, 132 (38), DOI: 10.1021/ja106052e, published Sep. 1, 2010, 2 pages.
Ding et al., *The Preparation of 3, 6-Bis(3-hexylthien-2-yl)-s-tetrazine and Its Conjugated Polymers*, Journal of Polymer Science Part A Polymer Chemistry, vol. 49, Issue 15, DOI: 10.1002/pola.24774, published online May 31, 2011, 13 pages.

* cited by examiner

QUATERNIZED TETRAZINE-BASED DONOR-ACCEPTOR COPOLYMERS

BACKGROUND

Renewable energy and materials is a rapidly growing field, the development of which is in higher demand than ever. One major branch of renewable energy is organic electronics and semiconducting materials. Organic semiconductors have several advantages over their silicon-based counterparts including renewability, their ability to be solution-processed into lightweight and flexible films, and their ability to have their properties easily tuned through chemical synthesis.

Important progress has been made towards making organic semiconductor technology ubiquitous in everyday uses. Technologies such as organic photovoltaics (OPVs) and organic batteries may provide a practical path to achieve low-cost, renewable energy harvesting, and storage. Plastic polymeric power generation and storage sources offer intriguing opportunities for both portable solar cells and batteries, as such materials are potentially flexible, lightweight, and easy to fabricate through low-cost processing techniques. Further, organic molecules may offer malleable properties that are easy to tune through chemical synthesis.

Typically, organic semiconducting materials (OSMs) are only soluble in organic solvents, and sometimes this solubility may be limited. This low solubility is mostly due to OSM designs having a highly planar nature that allows for optimal overlap of their pi-electron clouds and a high degree of crystallinity. The problem of solubility is typically dealt with by affixing alkyl side chains to the aromatic molecules that make up the polymer (or small molecule) backbone. Finding the appropriate side chain is unique to each new donor-acceptor polymer system that is designed, and certain chains lengths and chain branching works better for some systems than others. This delicate balance between solubility and planarity can make for long and arduous molecular designing to obtain the ideal material.

The vast majority of polymers that have been successfully used in OPVs are comprised of an alternating electron-rich (donor) and electron-deficient (acceptor) co-monomers, called donor-acceptor (D-A) copolymers. Typically, it is much easier, for synthetic reasons, to affix alkyl chains to the donor molecules. For this reason, the library of known donor molecules is much more diverse than that of the acceptor molecules. There exists a need for acceptors that can also positively affect solubility.

SUMMARY

According to an embodiment, a quaternized tetrazine-based donor-acceptor (D-A) copolymer is disclosed.

According to another embodiment, an organic photovoltaic device is disclosed. The organic photovoltaic device comprises an active layer that includes a quaternized tetrazine-based donor-acceptor (D-A) copolymer.

According to another embodiment, a process of forming a quaternized tetrazine-based donor-acceptor (D-A) copolymer is disclosed. The process includes forming a quaternized tetrazine monomer and polymerizing the quaternized tetrazine monomer and a donor molecule to form the quaternized tetrazine-based D-A copolymer.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes quaternized tetrazine-based donor-acceptor (D-A) copolymers and methods of forming the quaternized tetrazine-based D-A copolymers. In the present disclosure, the incorporation of an acceptor molecule may provide the ability to impart not only good solubility, but also solubility in a broad array of solvents. Such solvents may include typical options such as chloroform, chlorobenzenes, dimethylformamide (DMF), toluene, and tetrahydrofuran (THF), but may also include polar protic solvents such as water, ethanol, and isopropanol. Such solubility characteristics may be imparted by using an electron deficient, anionic moiety, whereby switching the counter cations may enable alteration of a solubility profile.

In some cases, as described further herein, the quaternized tetrazine-based D-A copolymers of the present disclosure may be utilized to fabricate an OPV device. The OPV device fabrication may be done as blends with organic molecules as is typical for OPV devices, or with inorganic molecules such as perovskites (which is atypical for OPV devices), by taking advantage of the variable solubility profile afforded to the polymer by the nature of the counter cations. The potential for solubility in polar protic solvents also allows these D-A copolymers to be fabricated orthogonally with other organic layers. This orthogonal processability represents another advantage associated with the quaternized tetrazine-based D-A copolymers of the present disclosure.

Figure 1A:
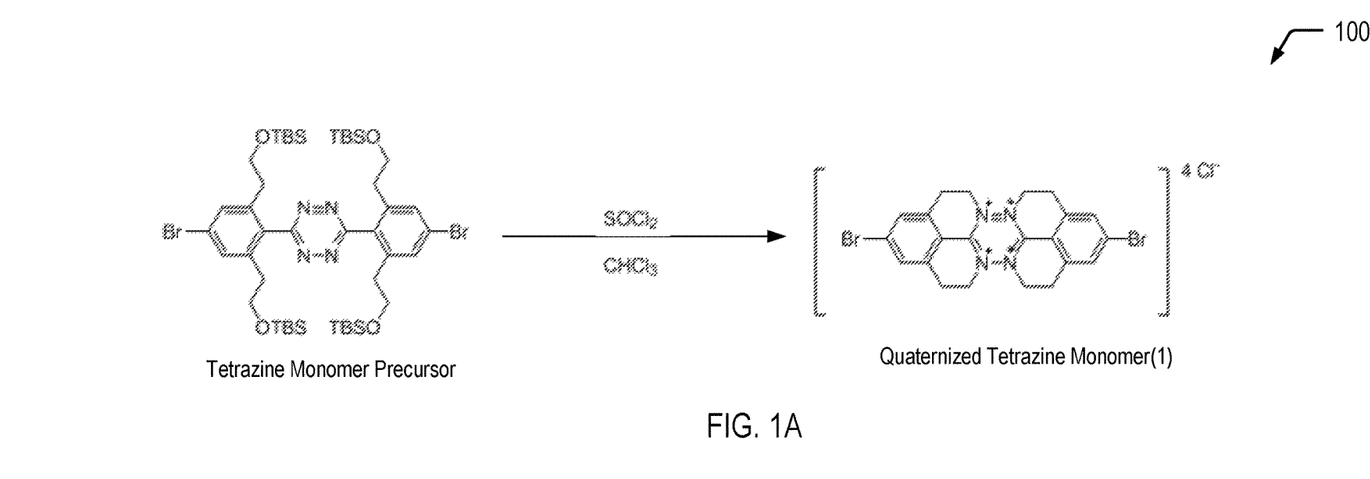
FIG. 1A is a chemical reaction diagram illustrating the formation of a quaternized tetrazine monomer, according to one embodiment.
Figure 1B:
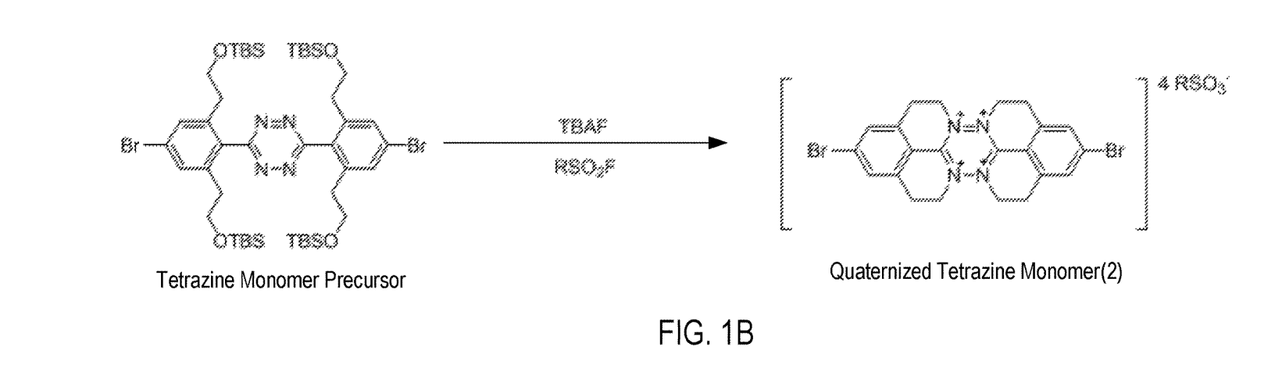
FIG. 1B is a chemical reaction diagram illustrating the formation of a quaternized tetrazine monomer, according to one embodiment.

Referring to FIGS. 1A and 1B, a diagram 100 depicts illustrative examples of processes of forming quaternized tetrazine monomers for use in forming the quaternized tetrazine-based D-A copolymers of the present disclosure. In FIG. 1A, a tetrazine monomer precursor is utilized to form a first quaternized tetrazine monomer (identified as "Quaternized Tetrazine Monomer(1)" in FIG. 1A). In FIG. 1B, the tetrazine monomer precursor is utilized to form a second quaternized tetrazine monomer (identified as "Quaternized Tetrazine Monomer(2)" in FIG. 1B). In some cases, the tetrazine monomer precursor depicted in FIGS. 1A and 1B may be formed according to the example processes described further herein with respect to FIGS. 6A-6B, FIG. 7, and FIG. 8.

FIGS. 1A and 1B illustrate that the tetrazine monomer precursor may be reacted with either thionyl chloride or an alkylsulfonyl fluoride (where the alkyl chains can be selected from C4-C20 in length, linear or branched) via simultaneous nucleophilic substitution conditions of the tetrazine imines at the carbons bonded to the TBS-protected hydroxyl groups. The result is a tetra-quaternized tetrazinium monomer. Selecting the reagents and conditions of the nucleophilic substitutions results in different counter cations which affect the solubility of the monomers and any resulting polymers synthesized from the monomers. Using thionyl chloride (as depicted in FIG. 1A) results in a water soluble polymer (among other solvents). Using the alkylsulfonyl fluoride chemical (as depicted in FIG. 1B) results in four counter cations with alkyl sulfides where the alkyl chains of the monomer can be selected to promote solubility in common organic solvents.

Figure 2:
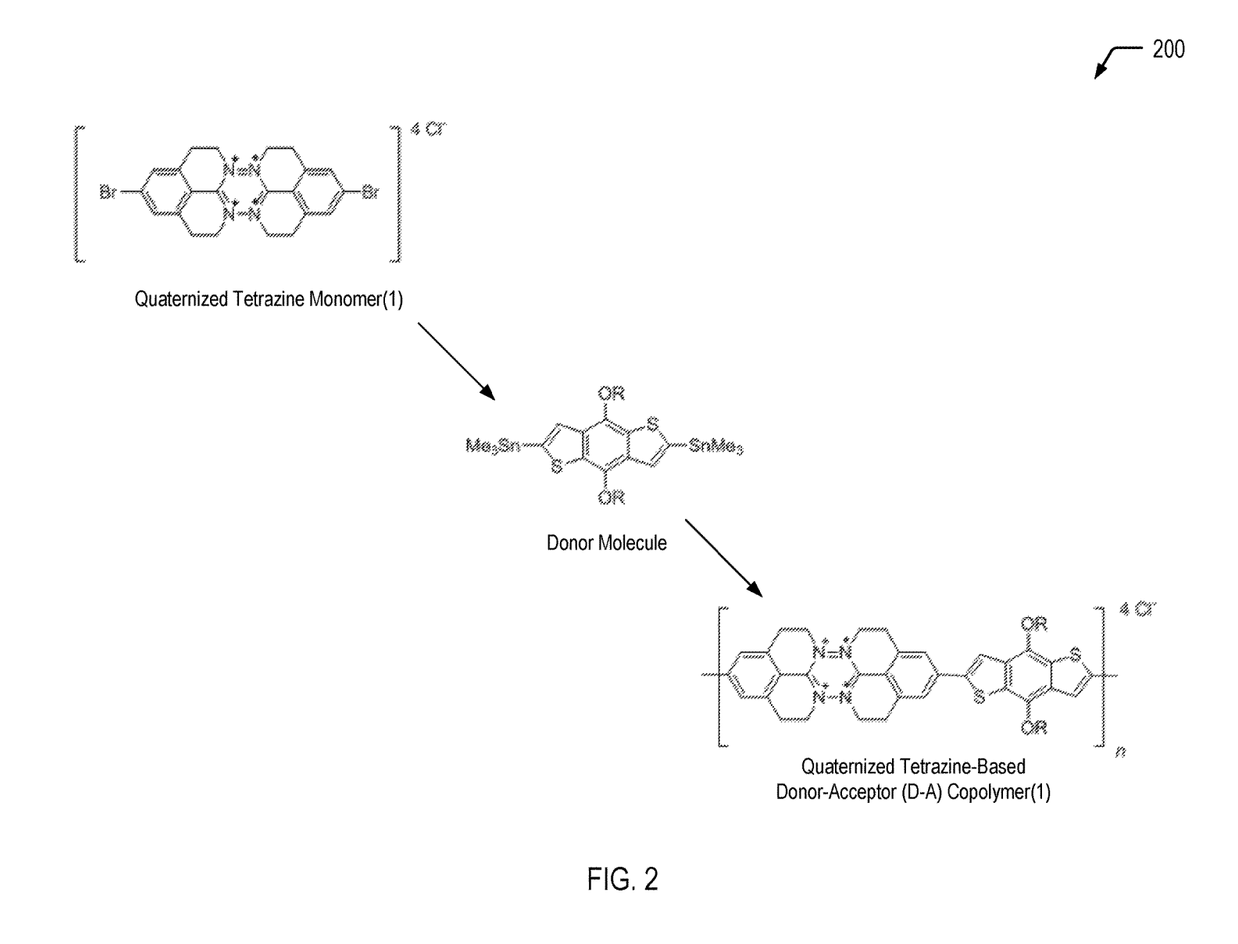
FIG. 2 is a chemical reaction diagram illustrating the formation of a quaternized tetrazine-based donor-acceptor (D-A) copolymer, according to one embodiment.
Figure 3:
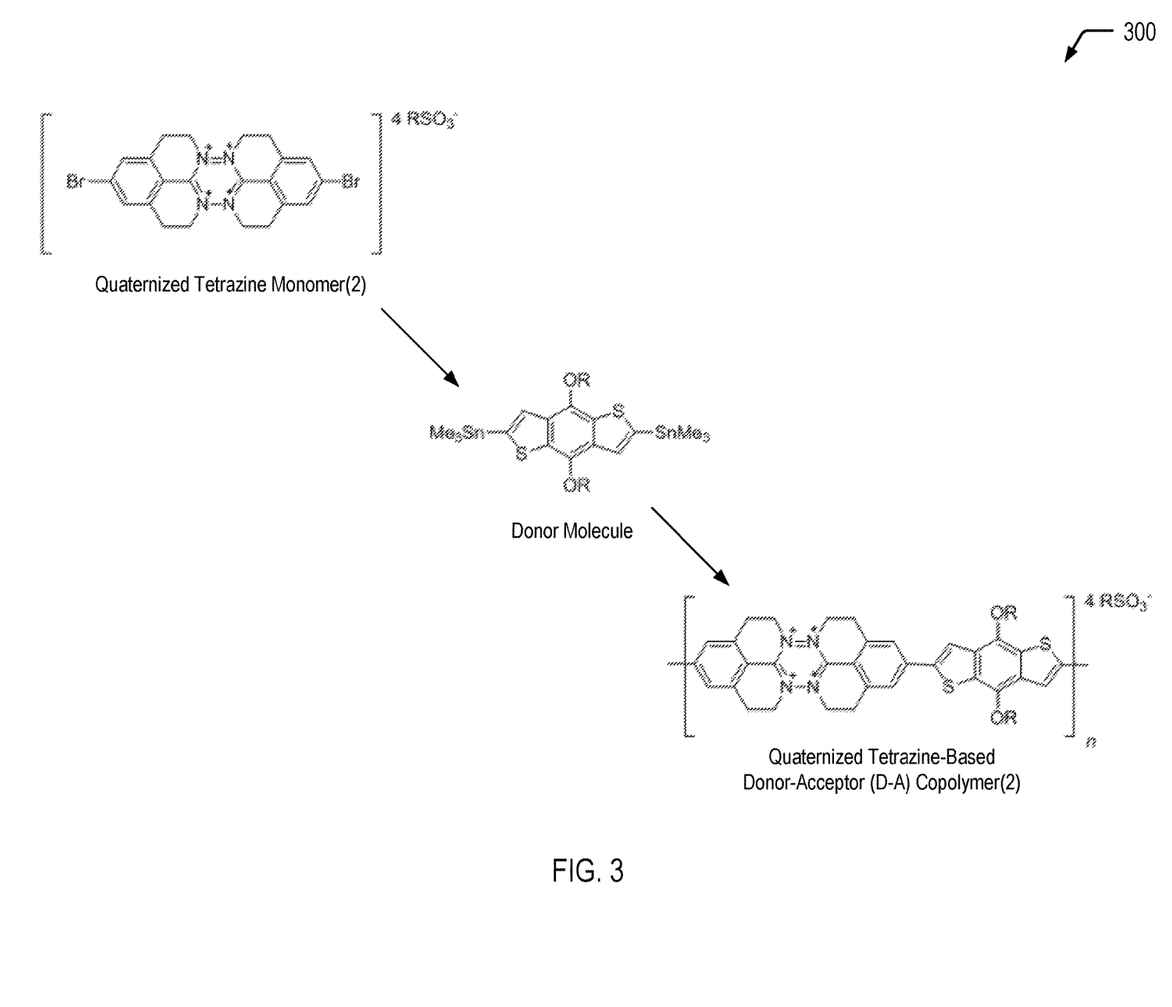
FIG. 3 is a chemical reaction diagram illustrating the formation of a quaternized tetrazine-based donor-acceptor (D-A) copolymer, according to one embodiment.

In FIG. 1A, the first quaternized tetrazine monomer is synthesized using thionyl chloride to give a tetra-chloride version of a quaternized tetrazine monomer for subsequent polymerization with a donor molecule to form a quaternized tetrazine-based D-A copolymer (as depicted in FIG. 2). In FIG. 1B, the second quaternized tetrazine monomer is synthesized via TBAF and an alkylsulfate fluoride compound (depicted as "RSO$_2$F" in FIG. 1B) to form an alkylate sulfite version of a quaternized tetrazine monomer for subsequent polymerization with a donor molecule to form a quaternized tetrazine-based D-A copolymer (as depicted in FIG. 3).

Prophetic Example: Formation of Quaternized Tetrazine Monomer(1)

To a solution of the tetrazine in an organic solvent which may include acetonitrile, chloroform, chlorobenzene, etc. may be added thionyl chloride, and the reaction mixture may be stirred at room temperature for 24 hours. The solvents may be removed in vacuo, and the resulting solid residue may be washed with solvents which may include methanol and DMF. The crude solid may be recrystallized from a mixture of solvents that may include water, methanol, ethanol, and/or acetone.

Prophetic Example: Formation of Quaternized Tetrazine Monomer(2)

To a solution of the tetrazine in an organic solvent which may include acetonitrile, chloroform, chlorobenzene, etc. may be added an alkylsulfite fluoride and a 1 M solution of TBAF in THF, and the reaction mixture may be stirred at reflux for 24 hours. The reaction may be cooled to room temperature and may be precipitated into hexane, and filtered. The crude solid may be recrystallized from a mixture of solvents that may include methanol, ethanol, and/or acetone, hexane, dichloromethane, chloroform.

Thus, FIGS. 1A and 1B depict examples of processes of forming quaternized tetrazine monomers. As described further herein with respect to FIG. 2, FIG. 3, FIGS. 4A and 4B, and FIGS. 5A and 5B, the quaternized tetrazine monomers depicted in FIGS. 1A and 1B may be utilized to form quaternized tetrazine-based D-A copolymers. In some cases, the quaternized tetrazine-based D-A copolymers formed from the quaternized tetrazine monomers depicted in FIGS. 1A and 1B may be fabricated into OPV devices.

Referring to FIG. 2, a chemical reaction diagram 200 depicts an example of a process of utilizing the first quaternized tetrazine monomer depicted in FIG. 1A to form a first quaternized tetrazine-based D-A copolymer (identified as "Quaternized Tetrazine-Based D-A Copolymer(1)" in FIG. 2).

FIG. 2 illustrates that the first quaternized tetrazine monomer of FIG. 1A may be polymerized with donor (electron rich) molecules by cross-coupling conditions. FIG. 2 depicts a non-limiting, illustrative example in which the donor (electron rich) molecule is alkoxy-BDT bistrimethylstannane. In other embodiments, alternative and/or additional donor molecules may be utilized.

Prophetic Example: Formation of Quaternized Tetrazine-Based D-A Copolymer(1)

An oven-dried, Schlenk flask may be charged with dry, deoxygenated toluene (5-10 mL), dibromobisphenyltetrazine monomer (1.0 equiv.), and a bisstannane-functionalized donor monomer (1.05 equiv.). The stirred solution may be sparged with argon for 10 minutes and may be followed by the addition of tris(dibenzylideneacetone)dipalladium(0) (2 mol %) and tri(o-tolyl)phosphine (8 mol %). The reaction mixture may be heated to reflux and stirred, under argon, for 4-96 hours. The polymer may be end-capped by the subsequent addition of an excess amount of trimethyl(phenyl)tin and iodobenzene, each may be followed by up to a 4 hour period of reflux. The reaction mixture may be cooled to 50° C. and may be diluted with chloroform. A small portion of SiliaMetS® Cysteine may be added and the reaction mixture and may be followed by being stirred for 8 hours. The polymer may be precipitated into a cold, organic non-solvent such as methanol, acetone, or hexane and may be filtered. The polymer may be purified by any combination of Soxhlet extraction, reprecipitation, filtration, column chromatography, or other techniques.

Thus, FIG. 2 illustrates an example of a process of utilizing a quaternized tetrazine monomer to form a quaternized tetrazine-based D-A copolymer. As described further herein, the quaternized tetrazine-based D-A copolymer of FIG. 2 may be utilized to fabricate an OPV device. The OPV device fabrication may be done as blends with organic molecules as is typical for OPV devices, or with inorganic molecules such as perovskites (which is atypical for OPV devices), by taking advantage of the variable solubility profile afforded to the polymer by the nature of the counter cations. The potential for solubility in polar protic solvents also allows these D-A copolymers to be fabricated orthogonally with other organic layers. This orthogonal processability represents another advantage associated with the quaternized tetrazine-based D-A copolymers of the present disclosure.

Referring to FIG. 3, a chemical reaction diagram 300 depicts an example of a process of utilizing the second quaternized tetrazine monomer depicted in FIG. 1B to form a second quaternized tetrazine-based D-A copolymer (identified as "Quaternized Tetrazine-Based D-A Copolymer(2)" in FIG. 3).

FIG. 3 illustrates that the second quaternized tetrazine monomer of FIG. 1B may be polymerized with donor (electron rich) molecules by cross-coupling conditions. FIG. 3 depicts a non-limiting, illustrative example in which the donor (electron rich) molecule is alkoxy-BDT bistrimethylstannane. In other embodiments, alternative and/or additional donor molecules may be utilized.

Prophetic Example: Formation of Quaternized Tetrazine-Based D-A Copolymer(2)

An oven-dried, Schlenk flask may be charged with dry, deoxygenated toluene (5-10 mL), dibromobisphenyltetrazine monomer (1.0 equiv.), and a bisstannane-functionalized donor monomer (1.05 equiv.). The stirred solution may be sparged with argon for 10 minutes and may be followed by the addition of tris(dibenzylideneacetone)dipalladium(0) (2 mol %) and tri(o-tolyl)phosphine (8 mol %). The reaction mixture may be heated to reflux and stirred, under argon, for 4-96 hours. The polymer may be end-capped by the subsequent addition of an excess amount of trimethyl(phenyl)tin and iodobenzene, each may be followed by up to a 4 hour period of reflux. The reaction mixture may be cooled to 50° C. and may be diluted with chloroform. A small portion of SiliaMetS® Cysteine may be added and the reaction mixture and may be followed by being stirred for 8 hours. The polymer may be precipitated into a cold, organic non-solvent such as methanol, acetone, or hexane and may be filtered. The polymer may be purified by any combination of Soxhlet extraction, reprecipitation, filtration, column chromatography, or other techniques.

Thus, FIG. 3 illustrates an example of a process of utilizing a quaternized tetrazine monomer to form a quaternized tetrazine-based D-A copolymer. As described further herein, the quaternized tetrazine-based D-A copolymer of FIG. 3 may be utilized to fabricate an OPV device. The OPV device fabrication may be done as blends with organic molecules as is typical for OPV devices, or with inorganic molecules such as perovskites (which is atypical for OPV devices), by taking advantage of the variable solubility profile afforded to the polymer by the nature of the counter cations. The potential for solubility in polar protic solvents also allows these D-A copolymers to be fabricated orthogonally with other organic layers. This orthogonal processability represents another advantage associated with the quaternized tetrazine-based D-A copolymers of the present disclosure.

FIGS. 4A, 4B, 5A, and 5B depict alternative synthesis schemes in which the quaternized tetrazine-based D-A copolymers may be synthesized by first polymerizing the TBS-protected molecule with donor molecule(s) and then subjecting the resulting tetrazine-based copolymer to a post-polymerization quaternization of the tetrazine imines.

Figure 4A:
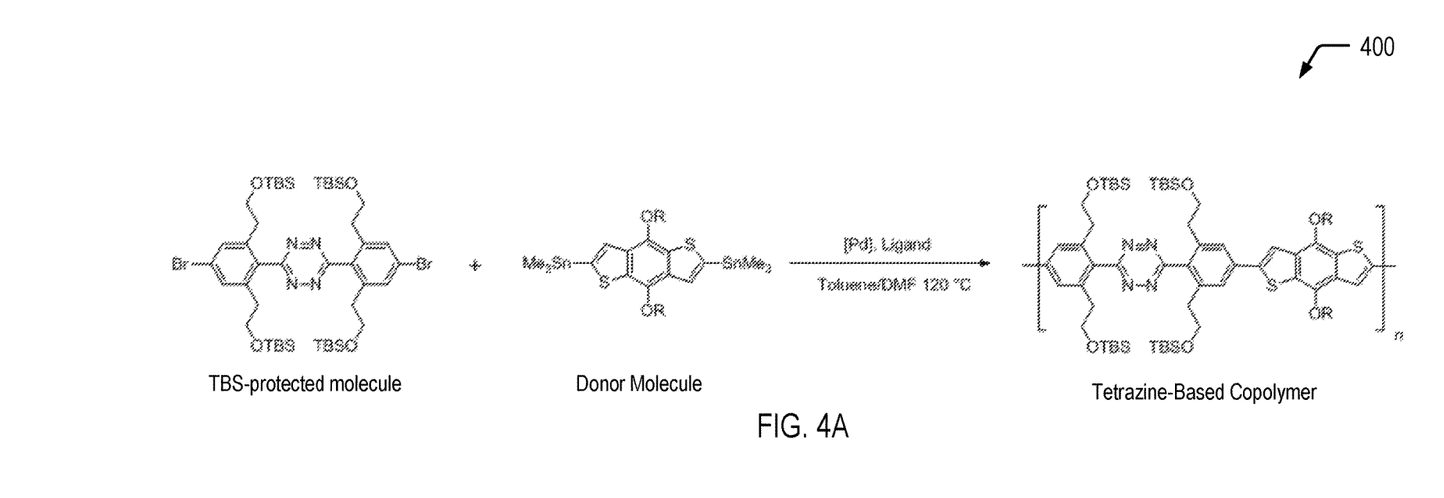
FIGS. 4A and 4B are chemical reaction diagrams illustrating the formation of a quaternized tetrazine-based donor-acceptor (D-A) copolymer, according to one embodiment.
Figure 4B:
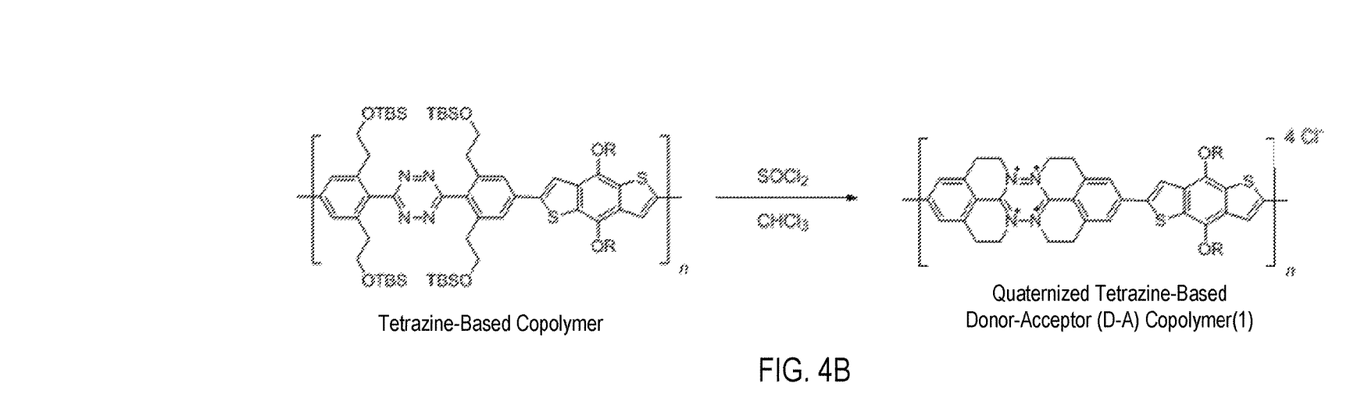

Referring to FIGS. 4A and 4B, a diagram 400 depicts an example of an alternative sequence of chemical reactions to form the first quaternized tetrazine-based D-A copolymer depicted in FIG. 2. FIG. 4A is a first chemical reaction diagram that illustrates an example process of forming a tetrazine-based copolymer, and FIG. 4B is a second chemical reaction diagram that illustrates an example of a process of utilizing the tetrazine-based copolymer to form the first quaternized tetrazine-based D-A copolymer.

With respect to the chemical reaction depicted in FIG. 4A, similar reaction conditions to those described above with respect to FIGS. 2 and 3 may be utilized to form the tetrazine-based copolymer from the TBS-protected molecule and the donor molecule. With respect to the chemical reaction depicted in FIG. 4B, similar reaction conditions to those described above with respect to FIG. 1A may be utilized to form the first quaternized tetrazine-based D-A copolymer.

Figures 5A, 5B:
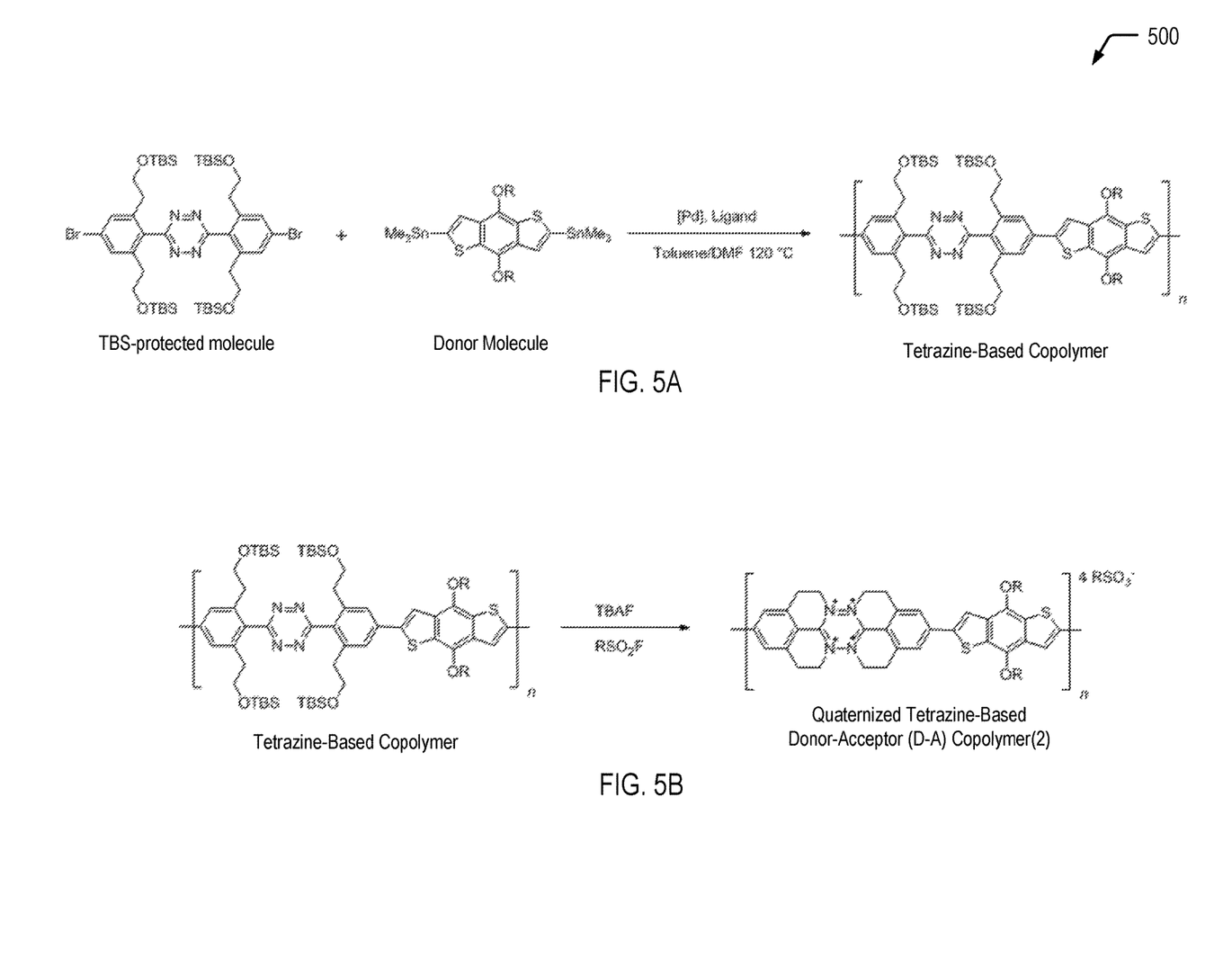
FIGS. 5A and 5B are chemical reaction diagrams illustrating the formation of a quaternized tetrazine-based donor-acceptor (D-A) copolymer, according to one embodiment.

Referring to FIGS. 5A and 5B, a diagram 500 depicts an example of an alternative sequence of chemical reactions to form the second quaternized tetrazine-based D-A copolymer depicted in FIG. 3. FIG. 5A is a first chemical reaction diagram that illustrates an example process of forming a tetrazine-based copolymer, and FIG. 5B is a second chemical reaction diagram that illustrates an example of a process of utilizing the tetrazine-based copolymer to form the second quaternized tetrazine-based D-A copolymer.

With respect to the chemical reaction depicted in FIG. 5A, similar reaction conditions to those described above with respect to FIGS. 2 and 3 may be utilized to form the tetrazine-based copolymer from the TBS-protected molecule and the donor molecule. With respect to the chemical reaction depicted in FIG. 5B, similar reaction conditions to those described above with respect to FIG. 1B may be utilized to form the second quaternized tetrazine-based D-A copolymer.

FIGS. 6A, 6B, 7, and 8 illustrate alternative example of processes for forming the tetrazine monomer precursor material depicted in FIGS. 1A and 1B. As described further herein, the proposed tetrazine-based monomers may be synthesized via alternative synthetic pathways starting from commercially available 5-bromo-2-iodo-1,3-dimethylbenzene. The tetrazine monomer precursors may be synthesized from either an aldehyde (which proceeds via a nitrile), a nitrile, or a Suzuki cross-coupling reaction. These precursors possess four tert-butyldimethylsiyl protected hydroxy groups (depicted as "OTBS" groups in FIGS. 6A, 6B, 7, and 8) which are then reacted with specific reagents that will cause a nucleophilic substitution to occur at each of the four imines on the central tetrazine ring. This results in a tetraquaternized tetrazinium monomer. Selecting the reagents and conditions of the nucleophilic substitutions results in different counter cations which affect the solubility of the monomer and any resulting polymers synthesized from the monomers. The tetrazinium monomer is polymerized with donor (electron rich) molecules by cross-coupling reactions.

Figure 6A:
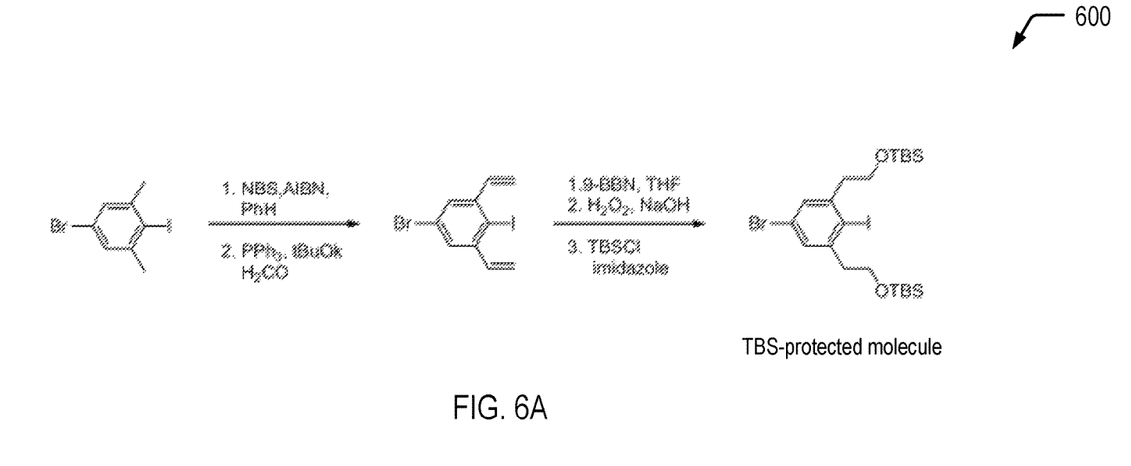
FIGS. 6A and 6B are chemical reaction diagrams illustrating the formation of the tetrazine monomer precursor depicted in FIGS. 1A and 1B, according to one embodiment.
Figure 6B:
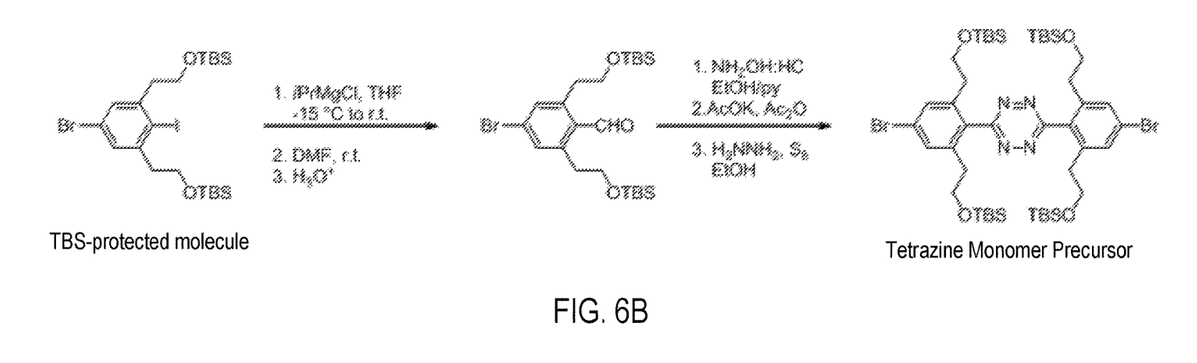

Referring to FIGS. 6A and 6B, a diagram 600 illustrates an example of a process of forming the tetrazine monomer precursor depicted in FIGS. 1A and 1B. FIG. 6A is a first chemical reaction diagram that depicts an example of a process of forming a TBS-protected molecule, and FIG. 6A is a second chemical reaction diagram that depicts an example of a process of utilizing the TBS-protected molecule to form the tetrazine monomer precursor depicted in FIGS. 1A and 1B. As described further herein with respect to FIGS. 1A and 1B, the tetrazine monomer precursor may be utilized to form either the first quaternized tetrazine monomer (depicted in FIG. 1A) or the second quaternized tetrazine monomer (depicted in FIG. 1B).

Prophetic Example: Synthesis of TBS-Protected Molecule

[First Chemical reaction depicted in FIG. 6A, identified as step 1]: 5-bromo-2-iodo-1,3-dimethylbenzene (1.0 equiv.), N-bromosuccinimide (>2.0 equiv.) was added to a stirred solution of AIBN (0.02 mol %) in benzene, DCM, Chloroform, or carbon tetrachloride at room temperature. The reaction mixture was heated to reflux and stirred for 5 hours, at which time the product had precipitated. The reaction mixture was allowed to cool to room temperature, and the product was filtered and washed with cold dichloromethane (5×100 mL). The white solid was dried in vacuo. The resulting white solid was used in the subsequent reaction without further purification.

[First Chemical reaction depicted in FIG. 6A, identified as step 2]: A solution of the product from the previous step (1.0 equiv.) and triphenylphosphine (2.5 equiv.) in dimethylformamide was heated at reflux for 18 hours. The solvent was removed, and the residue was dissolved in tetrahydrofuran, and an excess of paraformaldehyde was added. Potassium tert-butoxide (3.0 equiv.) in tetrahydrofuran was then transferred in the reaction vessel. The solvent was evaporated, and the residue was purified on a silica gel column with hexane as the eluent. Removal of solvent and recrystallization from absolute ethanol may also be used.

[Second Chemical reaction depicted in FIG. 6A, identified as steps 1 and 2]: 9-BBN (0.5 M in THF, 2.1 equiv.) was added dropwise over 30 min to a stirred and cooled (0° C.) solution of 1-iodo-4-bromo-2,6-divinylbenzene (8.68 g, 1.0 equiv.) in THF (125 mL). The ice bath was removed, and stirring was continued for 10 hours. The mixture was cooled to 0° C. and quenched by dropwise addition of MeOH. Aqueous NaOH (2 M, >1.5 equiv.) and 30% $H_2O_2$ (>10.0 equiv.) were poured into the stirred mixture. Stirring was continued for 2 h, and the mixture was extracted with $Et_2O$. The combined organic extracts were washed with brine, dried ($Na_2SO_4$), and the solvent was evaporated. The crude product was purified through column chromatography (silica gel, hexane/EtOAc=3/1).

[Second Chemical reaction depicted in FIG. 6A, identified as step 3]: The tetrahydroxy product from the previous step (1.0 equiv.) and a catalytic amount of imidazole were dissolved in an organic solvent such as DCM. Tert-butyldimethylsilyl chloride (>2.0 equiv.) was added in one portion to the reaction and the mixture was stirred at room temperature until completion. The reaction was washed with water, brine, and the organic layer was dried over $MgSO_4$. The solvents were removed in vacuo and the crude product may be purified via recrystallization, column chromatography, or by techniques known to those skilled in the arts.

Prophetic Example: Synthesis of Tetrazine Monomer Precursor

[First Chemical reaction depicted in FIG. 6B, identified as steps 1-3]: A solution of the compound from the previous (1.0 equiv.) in dry THF may be sparged with Argon. The solution may be cooled to −15° C., i-PrMgCl (2M in THF, 1.05 equiv.) may be added and the reaction may be stirred for 2 hours at −15° C. Then, dry DMF (14.24 mmol, 1.1 mL) may be added and the reaction may be allowed to warm over 1 hour. The reaction mat be quenched with aqueous 1M HCl and extracted with diethyl ether. The organic layer may be washed with brine, dried over anhydrous sodium sulfate, filtered, and concentrated. The resulting crude may be purified by flash chromatography on silica gel.

[Second Chemical reaction depicted in FIG. 6B, identified as steps 1 and 2]: A mixture solution of the aldehyde from the previous step (1.0 equiv.) and hydroxylamine hydrochloride salt (1.5 equiv.) in pyridine/ethanol (1:1 v/v) was stirred at 80° C. overnight. Then the solvent was removed in vacuo. The residue was dissolved in chloroform (100 mL), and the solution was washed with distilled water (2×50 mL) and dried over anhydrous magnesium sulfate. The solvent was removed in vacuo, and the viscous residue was dissolved in acetic anhydride containing catalytic potassium acetate and then refluxed for 3 hours. The mixture was poured into distilled water and extracted with hexanes (3×). The organic phase was washed with 5% aqueous sodium hydroxide solution and then water, dried over anhydrous magnesium sulfate before the solvent was removed in vacuo. The residue was purified by silica-gel column chromatography.

[Second Chemical reaction depicted in FIG. 6B, identified as step 3]: To a mixture of the nitrile from the previous step (1.0 equiv.) and sulphur (0.7 equiv.) in anhydrous ethanol was slowly added fresh hydrazine monohydrate (1.5 equiv.) at room temperature. The solution turned into yellow and large amount of gas evolved. The solution was heated up to reflux and stirred for 2 hours and was cooled down to room temperature. Crystals were allowed to form in solution, were collected by filtration and rinsed with cold ethanol before dried under vacuum. To a chloroform solution (50 mL) of the obtained solid, isoamyl nitrite (5.58 g, 2.0 equiv.) was added and the solution was stirred at room temperature overnight. The solvent was removed and the resulting red solid was washed with methanol twice before purified by silica-gel column chromatography.

Thus, FIGS. 6A and 6B illustrate an example of a process of forming a tetrazine monomer precursor that may be utilized in the synthesis of the quaternized tetrazine-based D-A copolymers of the present disclosure.

Figure 7:
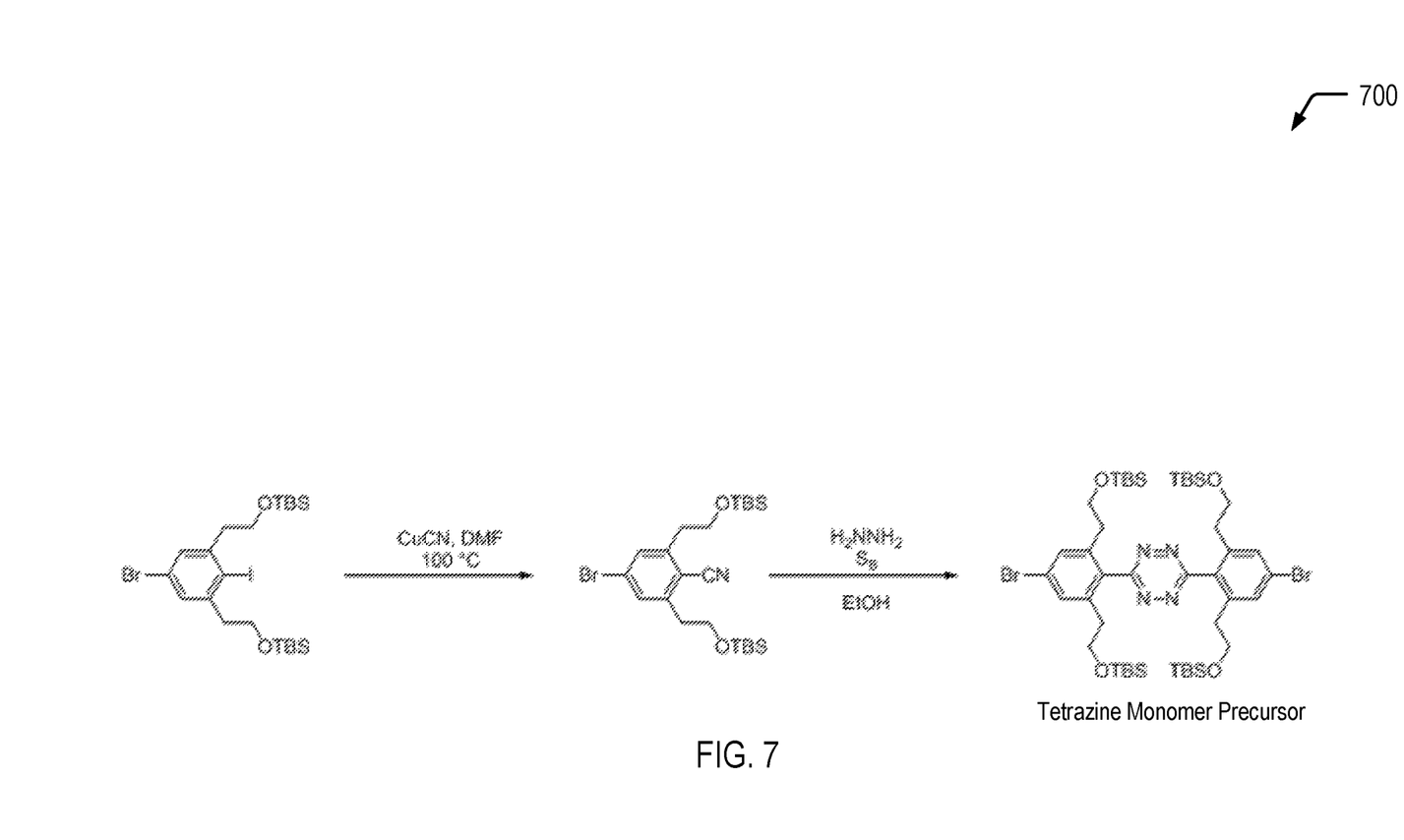
FIG. 7 is a chemical reaction diagram illustrating the formation of the tetrazine monomer precursor depicted in FIGS. 1A and 1B, according to one embodiment.

Referring to FIG. 7, a chemical reaction diagram 700 illustrates an alternative process of forming the tetrazine monomer precursor depicted in FIGS. 1A and 1B.

Prophetic Example: Synthesis of Tetrazine Monomer Precursor

[First chemical reaction depicted in FIG. 7]: The starting material (1.0 equiv.) was dissolved in of DMF and treated with 9.92 g (>1.0 equiv.) of CuCN. The system may be flushed with nitrogen, after which the mixture warmed to 100° C. and stirred for 18 hours. The mixture was allowed to cool to room temperature, and any precipitates were removed via filtration and washed with ethyl acetate. The combined organics were diluted with water and then extracted with ethyl acetate (2×). The combined layers were dried over sodium sulfate, filtered, and evaporated to dryness. Additional purification steps may be performed such as recrystallization or column chromatography (among other alternatives).

[First chemical reaction depicted in FIG. 7]: Similar reaction conditions utilized as described above with respect to step 3 of the second chemical reaction of FIG. 6B may be used to form the tetrazine monomer precursor.

Figure 8:
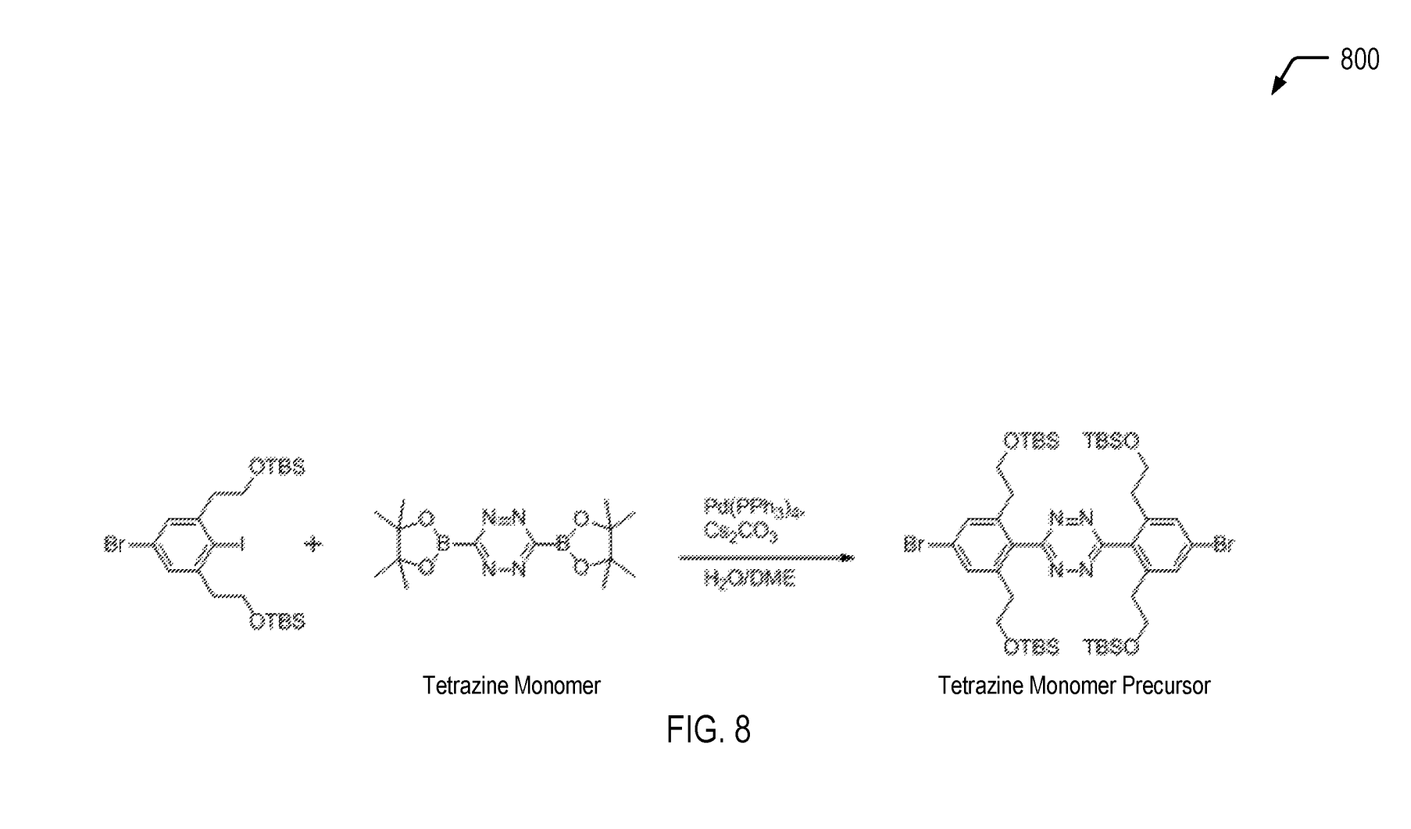
FIG. 8 is a chemical reaction diagram illustrating the formation of the tetrazine monomer precursor depicted in FIGS. 1A and 1B, according to one embodiment.

Referring to FIG. 8, a chemical reaction diagram 800 illustrates an alternative process of forming the tetrazine monomer precursor depicted in FIGS. 1A and 1B.

Prophetic Example: Synthesis of Tetrazine Monomer

To a solution of dibromo or dichlorotetrazine (1.0 equiv.) in DMF was added potassium acetate (3.0 equiv.), bis(pinacolato)diboron (>1.5 equiv.), and Pd(dppf)$Cl_2$ (5 mol %). The reaction mixture was stirred at 110° C. until completion. Brine (5 mL) was added, followed by EtOAc (10 mL). The layers were separated, and the organic layer was dried, filtered, and concentrated in vacuo.

Prophetic Example: Synthesis of Tetrazine Monomer Precursor

A reaction vessel may be charged with the phenyliodide (>2.0 equiv.), and the diboronic ester (1.0 equiv.), palladium catalyst (1-5 mol %) such as palladium acetate(II) or palladium tetrakis(triphenylphosphine), and a ligand such as tri(o-tolyl)phosphine (3-10 mol %). The atmosphere of the reaction vessel may be displaced with an inert gas such as nitrogen or argon. A degassed solvent mixture such dimethyl ether and aqueous solution of an alkaline base such as cesium carbonate (>2 equiv., 2.0 M) may be added to the reaction vessel. A phase transfer agent such as aliquat 336 may be added to the reaction mixture and the reaction mixture may be stirred at reflux for an extended period of time until the reaction is complete. The mixture may be allowed to cool to room temperature, and any precipitates may be removed via filtration and washed with ethyl acetate. The combined organics may be diluted with water and then extracted with ethyl acetate (2×). The combined layers may be dried over sodium sulfate, filtered, and evaporated to dryness. Additional purification steps may be performed such as recrystallization or column chromatography.

Figure 9:
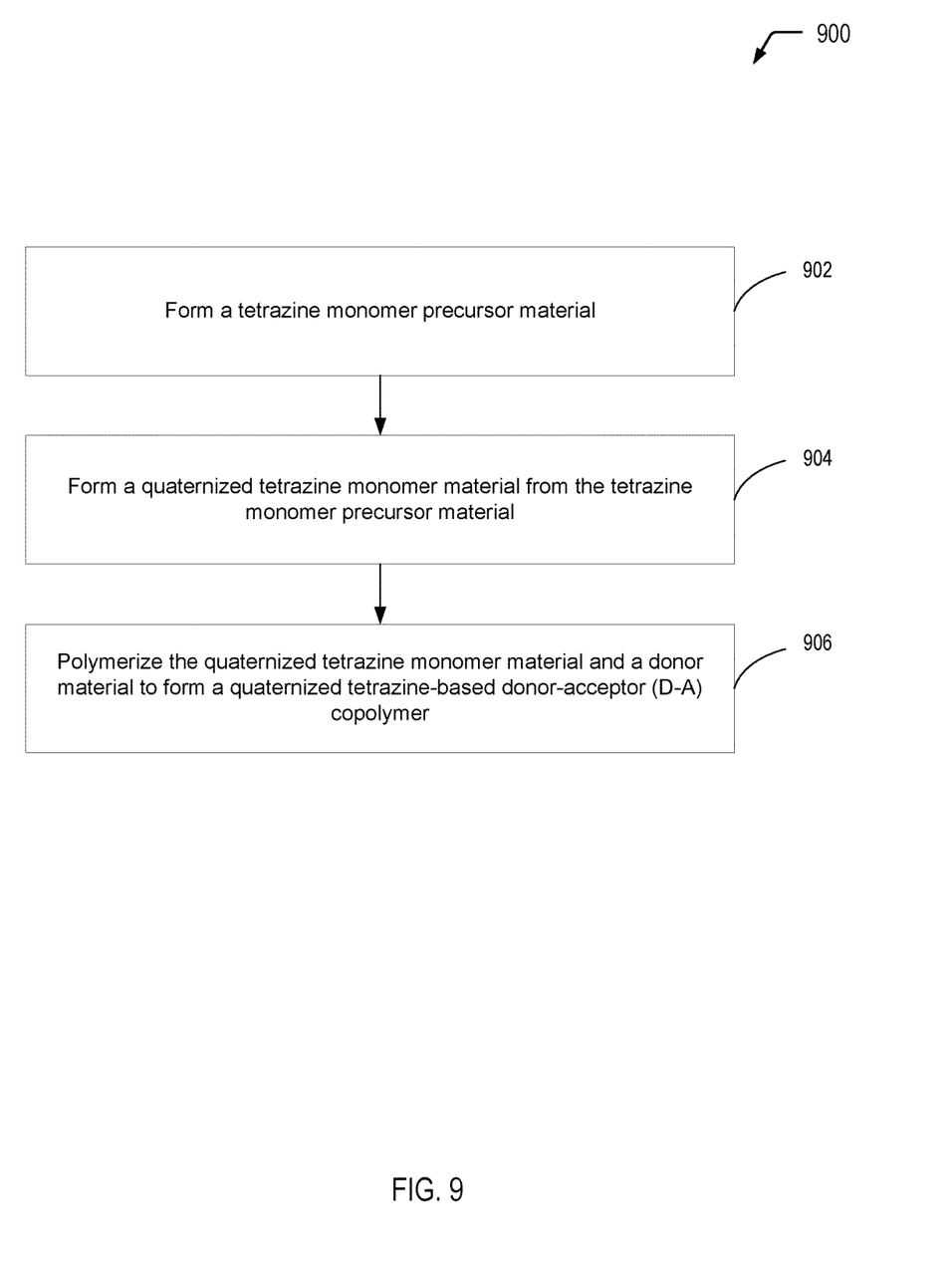
FIG. 9 is a flow diagram showing a particular embodiment of a process of forming a quaternized tetrazine-based donor-acceptor (D-A) copolymer.

Referring to FIG. 9, a flow diagram illustrates an exemplary process 900 of forming a quaternized tetrazine-based D-A copolymer, according to a particular embodiment. In the particular embodiment illustrated in FIG. 9, operations associated with forming a quaternized tetrazine monomer material are identified as operations 902-904, while operations associated with forming a quaternized tetrazine-based D-A copolymer are identified as operation 906. It will be appreciated that the operations shown in FIG. 9 are for illustrative purposes only and that the chemical reactions may be performed in alternative orders, at alternative times, by a single entity or by multiple entities, or a combination thereof. As an example, one entity may form the tetrazine monomer precursor material, and another entity may form the quaternized tetrazine monomer material, while another entity may form the quaternized tetrazine-based D-A copolymer. Further, alternative or additional entities may perform operations associated with forming the donor material(s) for polymerization with the quaternized tetrazine monomer material.

The process 900 includes forming a tetrazine monomer precursor material, at 902. For example, the tetrazine monomer precursor material depicted in FIGS. 1A and 1B may be formed according to the process described herein with respect to FIGS. 6A and 6B. As another example, the tetrazine monomer precursor material depicted in FIGS. 1A and 1B may be formed according to the process described herein with respect to FIG. 7. As a further example, the tetrazine monomer precursor material depicted in FIGS. 1A and 1B may be formed according to the process described herein with respect to FIG. 8.

The process 900 includes forming a quaternized tetrazine monomer material from the tetrazine monomer precursor material, at 904. For example, referring to FIG. 1A, the tetrazine monomer precursor material may be utilized to form the first quaternized tetrazine monomer material. As another example, referring to FIG. 1B, the tetrazine monomer precursor material may be utilized to form the second quaternized tetrazine monomer material.

The process 900 includes polymerizing the quaternized tetrazine monomer material and a donor material to form a quaternized tetrazine-based D-A copolymer, at 906. For example, referring to FIG. 2, the first quaternized tetrazine monomer material (depicted in FIG. 1A) may be polymerized with one or more donor (electron rich) molecules to form the first quaternized tetrazine-based D-A copolymer. As another example, referring to FIG. 3, the second quaternized tetrazine monomer material (depicted in FIG. 1B) may be polymerized with one or more donor (electron rich) molecules to form the second quaternized tetrazine-based D-A copolymer.

Thus, FIG. 9 illustrates an example of a process of forming a quaternized tetrazine-based D-A copolymer. In some cases, as described further herein with respect to FIG. 10, the quaternized tetrazine-based D-A copolymer(s) of the present disclosure may be utilized to form a portion of an OPV device.

Figure 10:
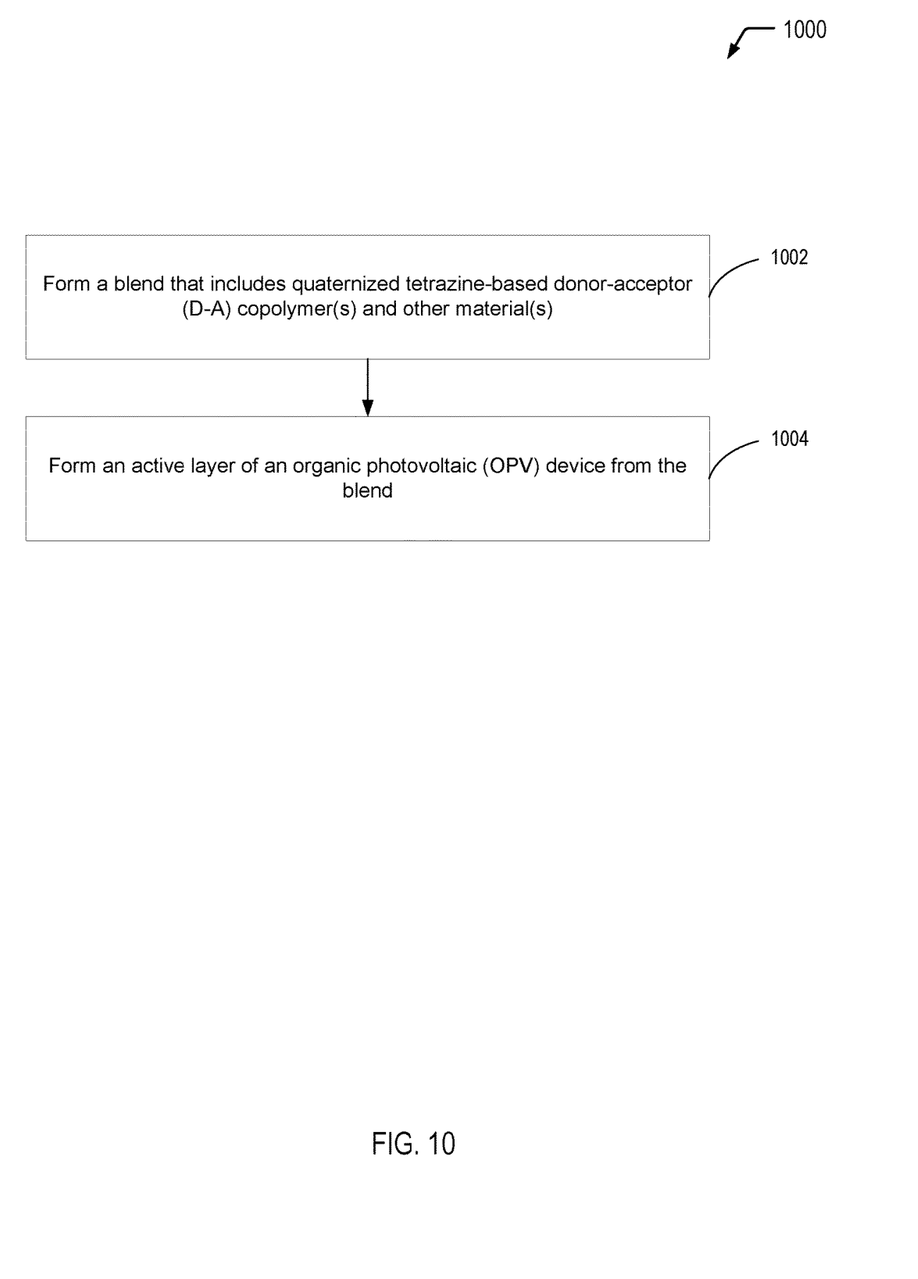
FIG. 10 is a flow diagram showing a particular embodiment of a process of forming an active layer of an organic photovoltaic (OPV) device that includes a quaternized tetrazine-based donor-acceptor (D-A) copolymer.

Referring to FIG. 10, a flow diagram illustrates an exemplary process 1000 of forming an active layer of an OPV device from a blend that includes the quaternized tetrazine-based D-A copolymer(s) of the present disclosure, according to one embodiment. While FIG. 10 depicts an example in which the quaternized tetrazine-based D-A copolymer(s) of the present disclosure are used as a component of an OPV device, it will be appreciated that the quaternized tetrazine-based D-A copolymer(s) of the present disclosure may be used in other contexts, such as organic batteries or organic sensors (among other alternatives).

In the particular embodiment illustrated in FIG. 10, operations associated with formation of a blend of materials that includes the quaternized tetrazine-based D-A copolymer(s) of the present disclosure are identified as 1002, while operations associated with formation of an active layer of an OPV device from the blend are identified as 1004. It will be appreciated that the operations shown in FIG. 10 are for illustrative purposes only and that the operations may be performed in alternative orders, at alternative times, by a single entity or by multiple entities, or a combination thereof. As an example, one entity may produce the quaternized tetrazine-based D-A copolymer(s), another entity (or entities) may produce the other material(s) for the blend, while another entity may mix the materials to form the blend. Further, alternative or additional entities may perform operations associated with forming the active layer of the OPV device from the blend.

The process 1000 includes forming a blend that includes a quaternized tetrazine-based D-A copolymer (or multiple quaternized tetrazine-based D-A copolymers) and one or more other materials, at 1002. The process 1000 also includes forming an active layer of an OPV device from the blend, at 1004. For example, the first quaternized tetrazine-based D-A copolymer depicted in FIGS. 2 and 4B and/or the second quaternized tetrazine-based D-A copolymer depicted in FIGS. 3 and 5B may be mixed with one or more other materials to form a blend. As an example, the quaternized tetrazine-based D-A copolymer(s) of the present disclosure may represent a p-type material. In this case, the quaternized tetrazine-based D-A copolymer(s) may be mixed with one or more n-type materials that are suitable for use in an active layer of an OPV device. As described further herein, the quaternized tetrazine-based D-A copolymers of the present disclosure have desirable solubility characteristics, allowing for processing by common polar solvents, such as chloroform, chlorobenzenes, dimethylformamide, toluene, and THF. Further, the high ionic content of the quaternized tetrazine-based D-A copolymers of the present disclosure may allow for processing by polar protic solvents such as water, ethanol, and isopropanol.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A quaternized tetrazine-based donor-acceptor (D-A) copolymer comprising iminium cations.

2. The quaternized tetrazine-based D-A copolymer of claim 1 formed by a process comprising:
    forming a tetra-quaternized tetrazinium monomer comprising the iminium cations; and
    polymerizing the tetra-quaternized tetrazinium monomer and a donor molecule to form the quaternized tetrazine-based D-A copolymer.

3. The quaternized tetrazine-based D-A copolymer of claim 1, wherein the quaternized tetrazine-based D-A copolymer includes four chloride anions per polymeric repeat unit.

4. The quaternized tetrazine-based D-A copolymer of claim 3, wherein the quaternized tetrazine-based D-A copolymer is soluble in a polar protic solvent.

5. The quaternized tetrazine-based D-A copolymer of claim 3, wherein the quaternized tetrazine-based D-A copolymer is soluble in water.

6. The quaternized tetrazine-based D-A copolymer of claim 1, wherein the quaternized tetrazine-based D-A copolymer includes four alkyl sulfite anions per polymeric repeat unit.

7. The quaternized tetrazine-based D-A copolymer of claim 6, wherein the quaternized tetrazine-based D-A copolymer is soluble in a polar organic solvent.

8. The quaternized tetrazine-based D-A copolymer of claim 7, wherein the polar organic solvent includes chloroform, tetrahydrofuran (THF), dimethylformamide (DMF), chlorobenzene, dichlorobenzone, or a combination thereof.

9. The quaternized tetrazine-based D-A copolymer of claim 1 formed by a process comprising:
    forming a tetrazine-based copolymer that includes four tetrazine imines per polymeric repeat unit; and
    subjecting the tetrazine-based copolymer to a post-polymerization quaternization of each of the four tetrazine imines to form the quaternized tetrazine-based D-A copolymer.

* * * * *